United States Patent [19]

Amano et al.

[11] 4,061,428
[45] Dec. 6, 1977

[54] SCANNING COLOR DENSITOMETER

[75] Inventors: Tadashi Amano; Masaji Nakamura, both of Hino, Japan

[73] Assignee: Konishiroku Photo Industry Co., Ltd., Tokyo, Japan

[21] Appl. No.: 697,535

[22] Filed: June 18, 1976

[30] Foreign Application Priority Data

June 21, 1975 Japan ................................. 50-76113

[51] Int. Cl.² .............................................. G01J 3/50
[52] U.S. Cl. .................................... 356/175; 250/226; 356/188; 356/203
[58] Field of Search ........ 250/226; 356/173, 175–177, 356/179, 186, 188, 189, 202, 203, 199

[56] References Cited

U.S. PATENT DOCUMENTS

| 3,614,241 | 10/1971 | Sanford | 356/175 |
| 3,851,170 | 11/1974 | Kitai | 356/188 A |
| 3,856,413 | 12/1974 | Bey et al. | 356/202 |

Primary Examiner—F. L. Evans
Attorney, Agent, or Firm—Martin A. Farber

[57] ABSTRACT

This invention relates to a scanning densitometer for obtaining information on the areal distribution of optical density of photographic image by scanning the entire area of an image, comprising plural input optical fiber bundles of which faces are arranged across the image and of which light-emitting faces are arranged on a circle with a predetermined interval. Plural output optical fiber bundles have light-receiving faces arranged so as to respectively face the light-emitting faces and which output faces are arranged so as to respectively face plural photoelectric converting elements. A rotary disc between the light-emitting faces and light-receiving faces is provided with blue, green and red filters arranged on the circle, whereby information of the distribution of photographic density over the entire image area being obtained by measuring the light which passes through said filters of said rotary disc.

8 Claims, 5 Drawing Figures

SCANNING COLOR DENSITOMETER

FIELD OF THE INVENTION

The present invention relates to a color photometric technology and more particularly to a scanning color densitometer adapted for use in a color printing device or in an analysis of color balance of a photographic image.

BACKGROUND OF THE INVENTION

In color printing devices for making color prints from color negative films, the optimum exposure for a color printing is generally determined by measuring the average photographic density of the entire area of a frame, that is, large area transmittance density (LATD). However, in case the subject to be printed contains a "subject failure", the printing method based on the LATD is unfavorable. The automatic color printers currently used in the market are provided with plural push-buttons for correction of density and color balance, and optimum and acceptable printing is achieved by an operator who visually identifies the character of the image to be printed therefrom and accordingly operates such correcting push-buttons.

However, such visual correcting procedure by an operator relies on the personal expertise of the operator and has been a problem in designing a completely automatic color printing machine. It has recently been tried, therefore, to obtain the information on the photographic density of the entire frame by means of a densitometer capable of scanning the entire area of image to be printed therefrom so that automatically estimating the image, specifically finding the presence of the subject failure from the information thus obtained is enabled, whereby printing is conducted in automatic mode to obtain positive image with high quality.

SUMMARY OF THE INVENTION

The principal object of the present invention is to provide a scanning color densitometer capable of furnishing the information on the distribution of photographic density, separated into blue, green and red components, over the entire area of an image.

An another object of the present invention is to provide a scanning color densitometer of a relatively simple and compact structure.

A still another object of the present invention is to provide a scanning color densitometer by which results of measurements can be easily calibrated in accordance with the variation in the brightness and/or color temperature of the light source for measurement.

According to the present invention, the above-mentioned objects can be achieved by a scanning color densitometer capable to obtaining information on the distribution of photographic densities by optically scanning substantially the entire area of an image, comprising plural input light-conducting members of which incident faces are arranged across the image being moved and which light-emitting faces are arranged on a circle, a rotary disc positioned so as to face said light-receiving faces and provided with plural blue, green and red filters in at least three windows which are formed on said circle on said rotary disc, photoelectric converters which receive the light through said filters from said light-emitting faces, a first detecting means for detecting the rotational position of said rotary disc and emitting a signal when said filter of a particular color becomes located in front of said light-emitting faces, and a second detecting means for detecting the rotational position of said rotary disc and releasing command for the density measurement when filters of any color become located in front of said light-emitting faces.

Furthermore the present invention is to provide a scanning color densitometer of the above-mention structure further comprising plural reference light conducting members of which incident faces are directed to the light source for the measurement and which light-emitting faces are arranged on said circle, a shutter plate provided between said light-emitting faces and said photoelectric converters and adapted to interrupt the light path between said reference light-conducting members and said photoelectric converters when said shutter plate is located in a first position and interrupt the light path between said first-mentioned light-conducting member and said photoelectric converters when said shutter plate is in a second position and said photoelectric converters adapted to receive the light from said reference light-emitting faces.

Still another objects and advantages of the present invention will be made apparent from the following description of preferred embodiments and the claims.

DETAILED DESCRIPTION OF THE PREFERRED EMBODIMENTS

Figure 1:
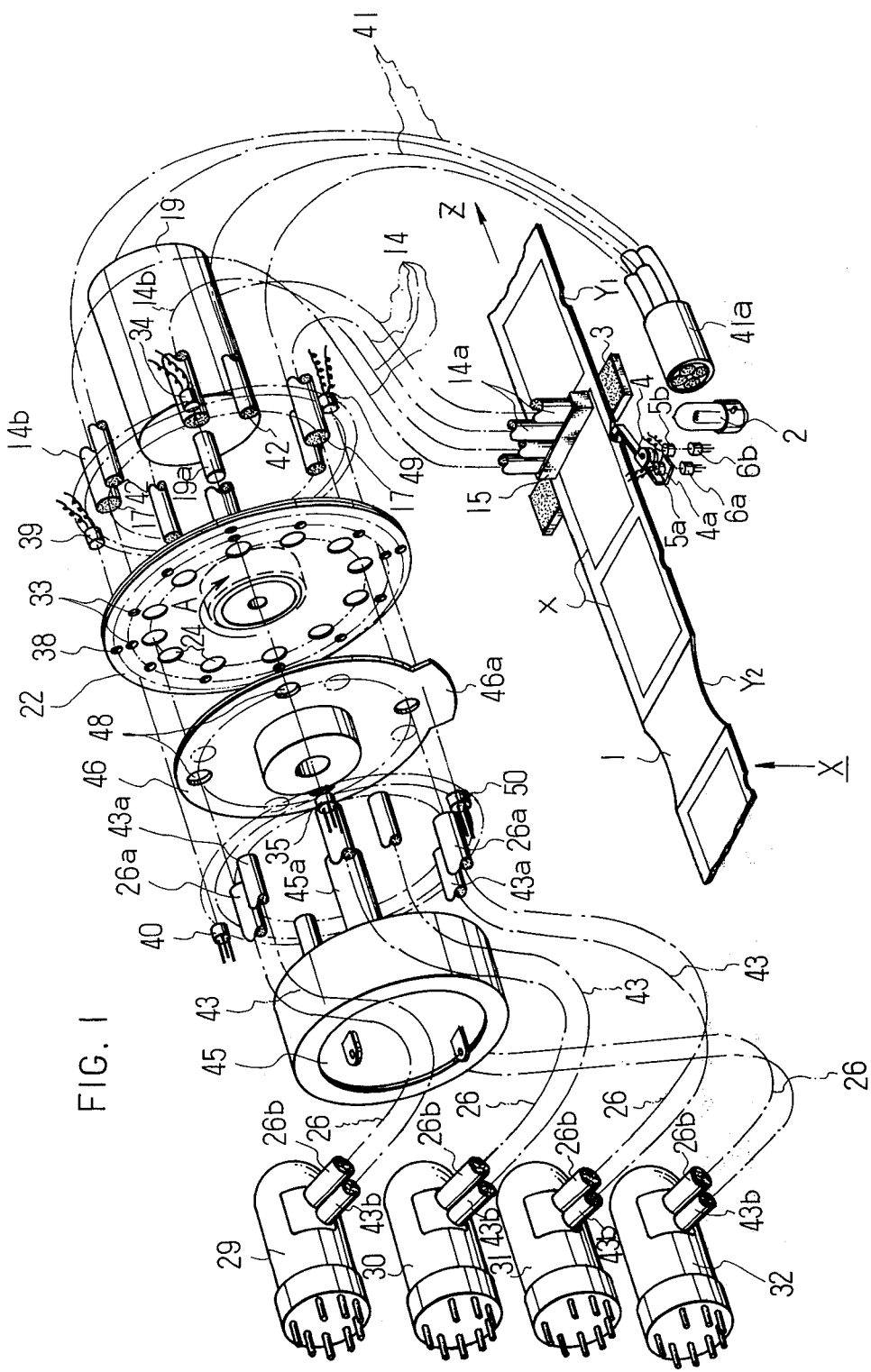
FIG. 1 is a partially omitted disassembled perspective view of the scanning color densitometer of the present invention.

Now referring to FIG. 1 showing the entire structure of the scanning color densitometer according to the present invention, a color negative film strip X is moved at a speed of about 80 to 200 mm/sec. The color negative film strip X is provided with notches Y1 on a side thereof, which serves to detect the position of the image frames $x$. A plurality of such film strips X are mutually connected by means of a splicing tape 1 which is provided on both sides thereof with splice notches Y2 which are deeper than said notches Y1. Along the path of said film strip X displaced in a direction indicated by an arrow Z, there is provided a feeler which engages with said notch Y1 when the leading end of an image frame $x$ becomes located on a diffuser 3 illuminated by a light source 2. Said feeler 4 is provided with a flap 4a integral therewith, and there are provided light-emitting diodes 5a, 5b and correspondingly located detectors such as phototransistors 6a, 6b in the moving range of said flap 4a in such a manner that the light path between said light-emitting diode 5a and phototransistor 6a is interrupted when the notch Y1 is detected by said feeler 4 and the light path between said light-emitting diode 5b and phototransistor 6b is interrupted when the notch Y2 is detected by said feeler 4. The functions of the signals from said phototransistors 6a, 6b will be clarified later by the description in connection with FIG. 4.

Figure 2:
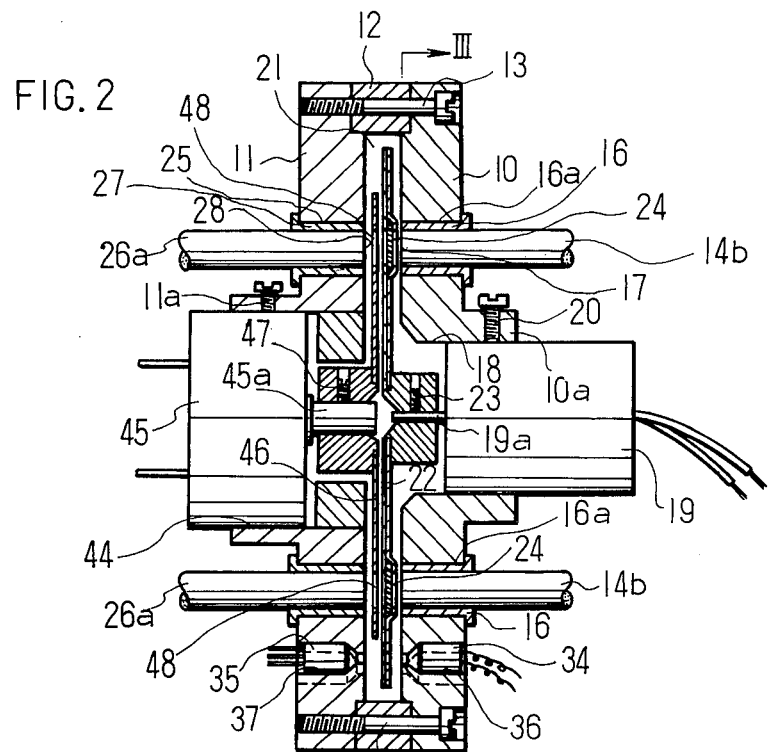
FIG. 2 is a cross sectional view of the principal part of the above-mentioned scanning color densitometer.

Now referring to FIG. 2, the scanning color densitometer of the present invention is constructed on a mounting plate 10, a mounting plate 11 provided facing thereto and a spacer frame 12 provided between said mounting plates 10, 11. Said mounting plates 10, 11 and said spacer frame 12 are mutually connected by means of screws 13 which are screwed into said mounting plate 11 through said mounting plate 10 and spacer frame 12.

Now again referring to FIG. 1, the scanning color densitometer of the present invention is provided with plural input light-conducting members 14 such as optical fiber bundles. In this embodiment, four bundles are provided. However, more or less bundles can be provided. The incident faces 14a of said optical fiber bundles are arranged on a straight line and maintained in a holding frame 15 which is elongated across said image frame x and above said diffuser 3 with a distance therefrom. Thus, as the color negative film X is advanced on said diffuser 3, the light diffused by said diffuser 3 is introduced into said optical fiber bundles 14 through a part of said image frame x.

Figure 3:
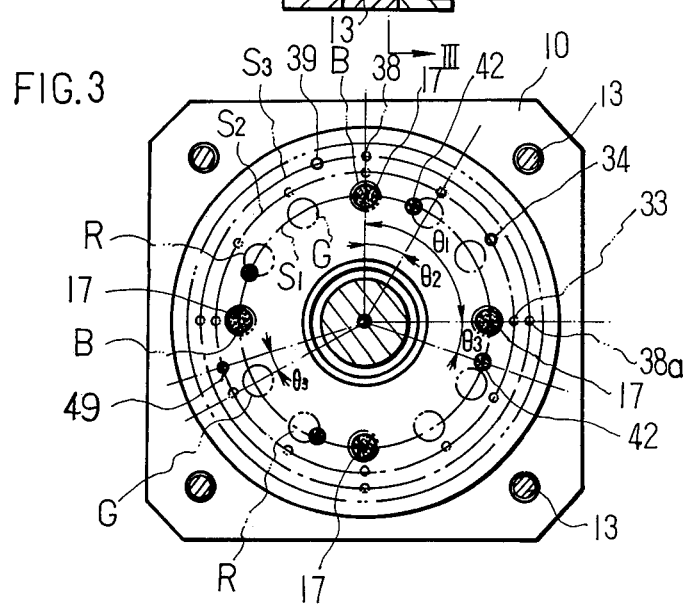
FIG. 3 is a cross sectional view along the line III—III in FIG. 2.

The ends of said optical fiber bundles 14 are mounted to said mounting plate 10 with a cylindrical plugs 16. Holes 16a of the plugs 16 are located along a circle S1 shown in FIG. 3 with a predetermined angular interval. Consequently the light-emitting faces 17 of said optical fiber bundles 14 are arranged with an angular interval of $\theta = 360°/N$. Wherein N is the number of such optical fiber bundles.

Said mounting plate 10 is provided, in the center of a boss 10a thereof, with a bore 18, into which there is inserted, and fixed by a screw 20 screwed into said boss 10a, a synchronous motor 19. A shaft 19a of the motor 19 is moved synchronously with the movement of the color negative film X. In a space 21 provided by said mounting plates 10, 11 and spacer frame 12 and shielded from the external light, a rotary disc 22 is mounted with a screw 23 on the drive shaft 19a of said synchronous motor 19. Said rotary disc 22, maintained in rotary motion in a direction indicated by the arrow A as shown in FIG. 1, is provided with at least three windows 24 on a circle having a diameter slightly larger than that of the circumscribed circle of said light-emitting face 17 arranged on the aforementioned circle S1. The rotary disc 22 is rotated with high speed of about 5,000 to 12,000 r.p.m. In order to increase the scanning speed of the image, however, it is advantageous to make the number of said windows 24 equal to 3N, with an angular interval of $\theta = 360°/3N$. Blue, green and red filters are mounted in these windows in cyclic order opposite to the direction of the arrow A. But said blue B, green G and red R filters may be arranged in any other cyclic order.

The aforementioned mounting plate 11 is provided, axially corresponding to said holes 16, with plural holes 25 into which there are respectively inserted cylindrical plugs 27. The ends 26a of plural output optical fiber bundles 26 are mounted to the mounting plate 11 with the plugs 27. Each light-receiving face 28 of said optical fiber bundles 26 is located so as to face a corresponding light-emitting face 17 thus allowing transmission of the density information to said optical fiber bundles 26 through said filters when either one of said filters B, G and R passes between said light-emitting face 17 and the light-receiving face 28. The output ends 26b of said optical fiber bundles 26 are respectively arranged toward light-receiving windows of plural photoelectric converting elements such as photomultipliers 29, 30, 31 and 32, by means of which the optical density information transmitted through said optical fiber bundles is converted into electric output.

Further referring to FIGS. 1 and 2, said rotary disc 22 is provided with detecting holes at 3N positions which are arranged on a circle S2 concentric with said circle S1. The detecting holes 33 are provided at the same angular positions as that of the windows 24. On stationary parts of the densitometer facing the moving path of said position detecting holes 33, there are provided a light-emitting diode 34 and a detector such as phototransistor 35 on the both sides of said rotary disc 22. Said light-emitting diode 34 and phototransistor 35 are respectively located in the holes 36, 37 provided in the mounting plates 10, 11. The detector 35 receives the light through the holes 33 from the light emitting diode 34 to produce signals for commanding measurment. Furthermore said rotary disc 22 is provided with holes 38 at N positions on a circle S3 concentric with said circle S2. The holes 38 are located on angular positions corresponding to these of the filters having a particular color, for example, blue. Holes 38a are provided on stationary parts of the densitometer facing the moving path of said holes 38. A light-emitting diode 39 and a detector 40 such as a phototransistor are provided on both sides of said rotary disc 22. The detector 40 receives the light from the light emitting diode 39 through the holes to produce signals which determine the color of the light being measured. Such color determination is given with regard to only one particular color because the color filters are arranged in a regular order, for example, blue-green-red.

There are also provided reference input optical fiber bundles 41 of a number equal to that of said input optical fiber bundles 14 in such a manner that the incident faces 41a thereof are located so as to face said light source 2 while the light-emitting faces 42 of said reference input bundles 41 are located on a plane in common with that of said light-emitting faces 17. In the illustrated embodiment said light-emitting faces 42 are located on said circle S1 but are respectively displaced from said light-emitting faces 17 by angle $\theta_3$. Such arrangement is however not compulsory. Furthermore there are provided reference output optical fiber bundles 43 of a same number N of which light-receiving faces 43a are supported by said mounting plate 11 so as to respectively correspond angularly to said light-emitting faces 42, while the output ends 43b of said reference output bundle 43 are guided to the light-receiving windows of afore-mentioned photomultipliers 29, 30, 31 and 32 to which each of the adjacent output optical fiber bundles 26 are connected. In the above-mentioned embodiment, outputs of the optical fiber bundles are transmitted to the photomultiplier through the optical fiber bundles 26 and 43. However, the optical fiber bundles 26 and 43 can be omitted. In such arrangement, the photomultipliers directly receives the light passed through the filters.

Said mounting plate 11 is provided in the center thereof with a bore 44 in which a rotary solenoid 45 is fixed by means of a screw 11a screwed into the boss. A shutter plate 46 of a diameter smaller than that of said circle S2 and parallel to said rotary disc is mounted by means of a screw 47 on the drive shaft 45a of said rotary solenoid 45 which is controlled by said phototransistor 6b for detecting aforementioned splice notch Y2. Said shutter plate 46 is provided with N openings 48 which are positioned on a circle the same as said circle S1 with an angular interval $\theta_1$ equal to that of said light-emitting faces 17 and which are of a diameter approximately equal to that of said windows 24. Said shutter plate 46 is adapted to assume either one of a first angular position and a second angular position which are mutually distanced by the angle $\theta_3$. Thus structured, said shutter plate 46 interrupts the light paths between the reference input optical fiber bundles 41 and the reference output optical bundles 43 in the first position thereof, and interrupts the light paths between the input optical fiber bundles 14 and the output optical fiber bundles 26 in the second position thereof. The light emitting diode 39 and the detector 40 are moved by the rotary solenoid 45 when the shutter is displaced to the second position. A light emitting diode 49 and a detector 50 such as phototransistor are mounted to stationary parts of the color densitometer, for example, to the mounting plates 10 and 11, so as to face each other with interposition of the disc 22. The light emitting diode 49 and the detector 50 are arranged on the circle S2 and at an angular position distanced from the position of the light emitting diode 39 and the detector 40 by $m\,\theta_2 + \theta_3$ wherein $m$ is a positive integer.

Figure 4:
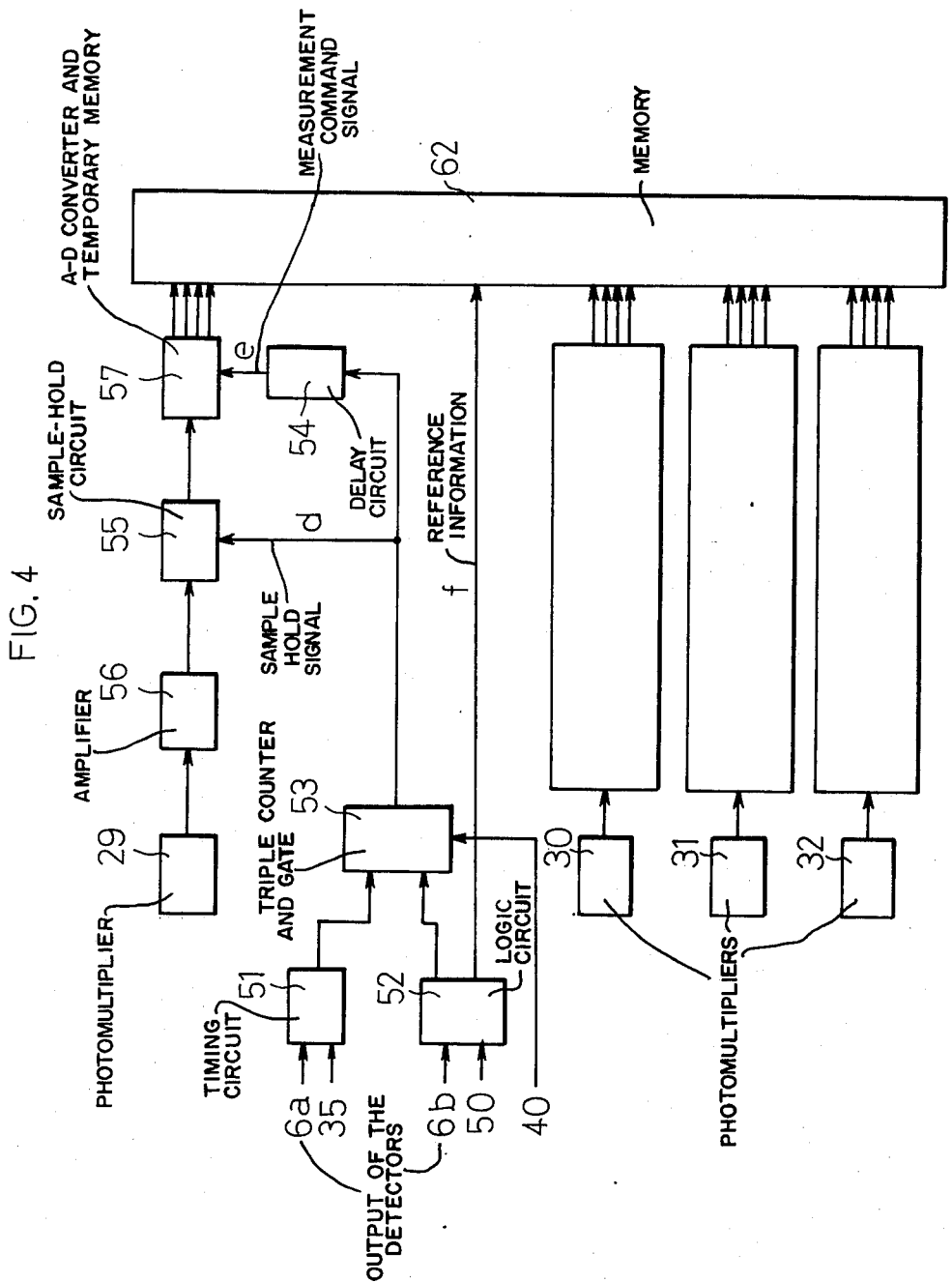
FIG. 4 is a diagram showing a logic sequence circuit for processing the signals obtained from the scanning color densitometer shown in FIG. 1–3.
Figure 5:
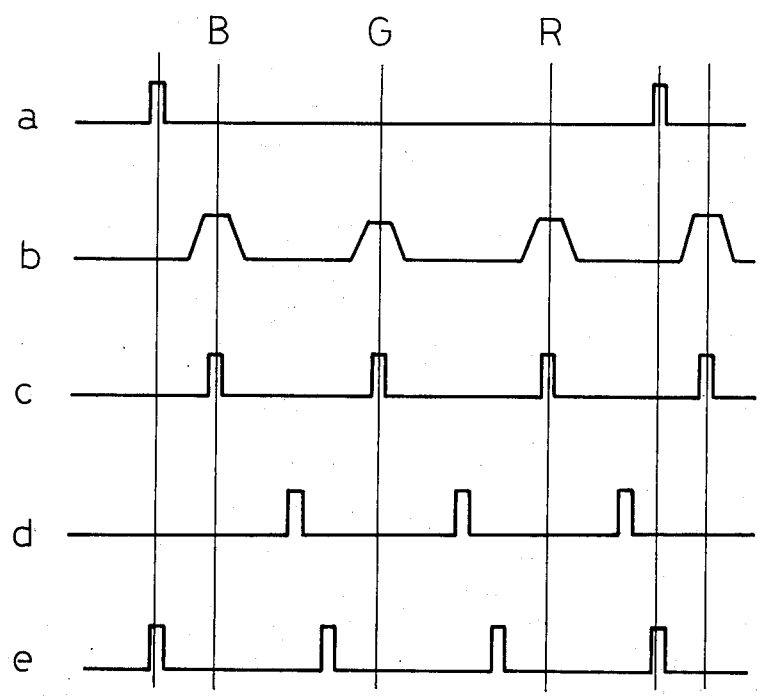
FIG. 5 is a time chart indicating the signals transmitted by said logic sequence circuit shown in FIG. 4 wherein $a$ is an output signal of detector 40, $b$ is an output signal of photoelectric converting element 29, $c$ is an output signal of position detector 35, $d$ is a sample hold signal, and $e$ is a measurment command signal.

Now the function of the scanning color densitometer of the present invention will be explained in the following while referring to FIG. 4 showing an embodiment of the signal processing circuit designed for the densitometer to be employed in a color printer. The output of the photomultiplier 29 is amplified by an amplifier 56 of which output is transmitted to a sample-hold circuit 55. The output of the amplifier 56 is held by the circuit 55 when the sample-hold command is generated by the circuit 53. Circuit 57 comprises a A-D (analogue to digital) converter and a temporary memory. The circuit 57 operates when measurment commands are transmitted from a delay circuit 54. When the leading end of an image frame $x$ is advanced to the diffuser 3, the feeler 4 engages with the notch Y1 and the detector 6a produce a signal. This signal is introduced to a timing circuit 51 which comprises a gate. The output of the detector 35 is also introduced to the timing circuit 51. The output of the detector 35 is transmitted to a circuit 53 through the timing circuit 51 only at the times having predetermined intervals. The starting point of the times is given by the signal from the detector 6a and the time interval is determined so that substantially the whole area of the frame is scanned. The circuit 53 comprises a triple counter and a gate. The triple counter serves to generate only three measurement commands respectively for color modes of blue, green and red. The outputs of the detector 6b and the output of the detector 50 are introduced to a logic circuit 52 which is analogous to that of the circuit 51. That is, the output of the detector 50 is transmitted to the circuit 53 through the circuit 52 when the output of the detector 6b is generated as the result of splice detection.

The circuit 53 generates a measurement command when the output from the circuits 51 or 52 is transmitted. This measurement command is modified by the output of the detector 40 by which color mode such as blue, green and red is specified. When the measurement command is transmitted to the sample hold circuit 55, the circuit 55 operates to hold the density information from the photomultiplier 29. A delay circuit 54 delays the measurement command so that a necessary time for the sample hold circuit 55 to generate the held sample is given. The circuit 57 operates when the measurement command from the delay circuit 54 is transmitted thereto to memorize the density information from the sample hold circuit 55 in digital mode. As the measurement command is modified by the output from the detector 40, the memorized density information in the circuit 57 is specified in color mode. The memorized information in circuit 57 is transmitted to a memory 62 which stores the density information. The output signal from the detector 29 concerning a reference light is stored in the memory 62 similar to the above-mentioned. Measuring and memorizing are performed under the control by the outputs of the detectors 6b and 50. Specifying with which mode of measurement of the density information and the reference information measurement is conducted is preformed by the signal transmitted through a line $f$ in FIG. 4. The reference information is used to correct the change of the density information due to the change of the light intensity of the light source 2. The outputs from the photomultipliers 30, 31 and 32 are processed and memorized in the memory 62 by the same circuit as the abovementioned.

What is claimed is:

1. A scanning color densitometer for measuring the areal distribution of the photographic densities of blue-light component, green-light component and red-light component separately by optically scanning substantially the entire area of an image, comprising
   plural light-conducting members having incident faces arranged across the image being moved and having light-emitting faces arranged on a first circle,
   a rotary disc positioned so as to face said light-emitting faces and having at least three windows formed therein on a second circle, said second circle being coaxial to and having substantially the same diameter as that of said first circle,
   plural blue, green and red filters mounted in said at least three windows, respectively,
   photoelectric converters disposed in optical paths defined by said filters and said light-emitting faces so as to receive the light through said filters from said light-emitting faces,
   a first detecting means for detecting the rotational position of said rotary disc and emitting a signal when said filters of a particular color become located in front of said light-emitting faces, and
   a second detecting means for detecting the rotational position of said rotary disc and releasing a command for the density measurement when any of said filters of any color become located in front of said light-emitting faces.

2. A scanning color densitometer according to claim 1, further comprising
   optical guide members operatively interposed between said rotary disc and said photoelectric converters having respective ends facing towards said light-emitting faces and said photoelectric converters, whereby the light through said filters from said light-emitting faces are transmitted to said photoelectric converters through said optical guide members, respectively.

3. A scanning color densitometer according to claim 1 wherein said rotary disc is formed with at least one hole on a third circle in a position corresponding to said filter of said particular color and at least three position detecting holes on a fourth circle in positions respectively corresponding to said blue, green and red filters, said first detecting means including a first light-emitting member and a cooperating first photoelectric member adapted to be mounted on stationary parts of the densitometer and positioned on both sides of said at least one hole, and said second detecting means including a second light-emitting member and a cooperating second photoelectric member positioned on both sides of said at least three position detecting holes.

4. A scanning color densitometer according to claim 2 wherein said light-conducting members and said optical guide members are composed of optical fiber bundles.

5. A scanning color densitometer according to claim 1 comprising plural reference light-conducting members having reference incident faces arranged adapted so as to face a light source for measurement and reference light-emitting faces arranged on said first circle, a shutter plate operatively moveably disposed between said light-emitting faces and said photoelectric converters so as to interrupt the light path between said reference light-conducting members and said photoelectric converters when said shutter plate is located in a first position thereof and so as to interrupt the light path between said first-mentioned light-conducting members and said photoelectric converters when said shutter plate is in a second position and said photoelectric converters are disposed in optical paths defined by said reference light-emitting faces so as to be adapted to receive the light from said reference light-emitting faces.

6. A scanning color densitometer according to claim 5, further comprising optical guide members interposed between said rotary disc and said photoelectric converters having respective ends facing towards said light-emitting faces and said photoelectric converters, whereby said optical guide members transmit the light from said reference light-emitting faces to said photoelectric converters, respectively.

7. A scanning color densitometer according to claim 6, wherein said reference light-emitting faces of said reference light-conducting members are positioned on said first circle on which said first-mentioned light-emitting faces of said light-conducting members are located but angularly displaced therefrom, and means for rotating said shutter plate within an angle approximately equal to the angle of displacement of said reference light-emitting faces relative to said first-mentioned light-emitting faces, and said shutter plate is formed with at least one opening located on said first circle.

8. A scanning color densitometer according to claim 3, wherein said first light-emitting member and said cooperating first photoelectric member as well as said second light-emitting member and said cooperating second photoelectric member are positioned, respectively in axial direction parallel to the axis of said rotary disc.

* * * * *